United States Patent [19]

Roper et al.

[11] Patent Number: 4,458,528
[45] Date of Patent: Jul. 10, 1984

[54] STICKOMETER

[75] Inventors: Wilbur F. Roper, DeSoto; Fletcher J. Williams, Dallas; V. Roy Slover, Irving, all of Tex.

[73] Assignee: Mobil Oil Corporation, New York, N.Y.

[21] Appl. No.: 454,782

[22] Filed: Dec. 30, 1982

[51] Int. Cl.³ .............................................. E21B 49/10
[52] U.S. Cl. .................................................... 73/151
[58] Field of Search ....................................... 73/151

Primary Examiner—Howard A. Birmiel
Attorney, Agent, or Firm—Alexander J. McKillop; Michael G. Gilman; Charles J. Speciale

[57] ABSTRACT

An improved instrument for measuring the relative "stickiness" of a drilling mud under well drilling condition is disclosed. It features a filtration member comprised of the material of the formation within which the well is drilled. After formation of a filter cake on the surface of the stone filtration member, a plunger is juxtaposed to the stone filtration member and the amount of torque required to rotate the plunger with respect thereto after juxtaposition for a fixed period of time is measured, to provide a relative indication of the adhesion of the plunger to the stone.

10 Claims, 7 Drawing Figures

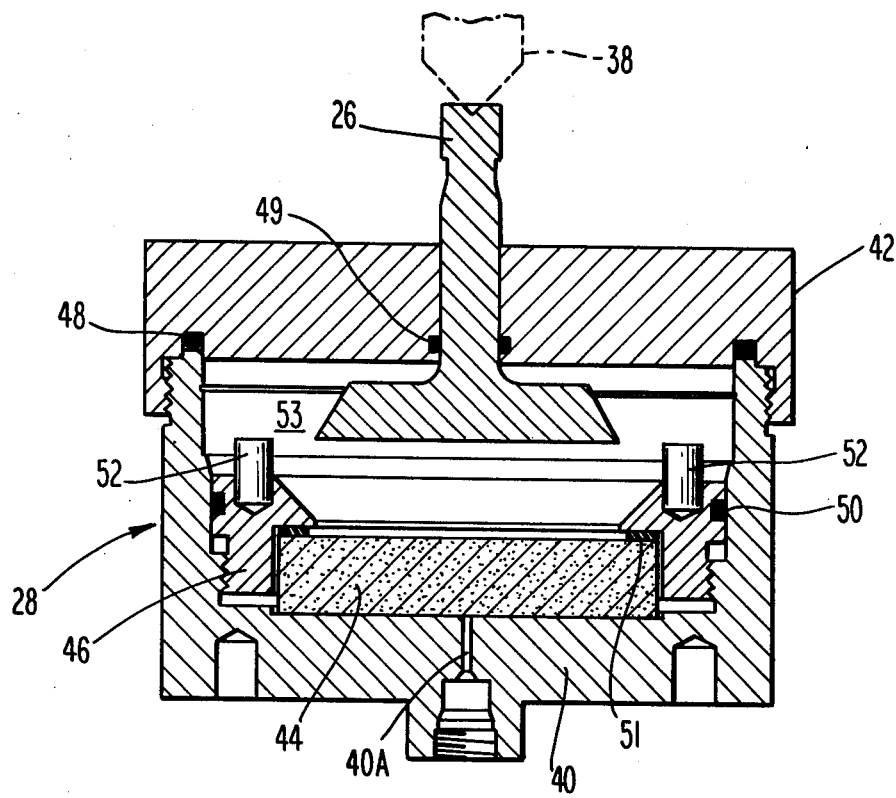
*Fig. 5*
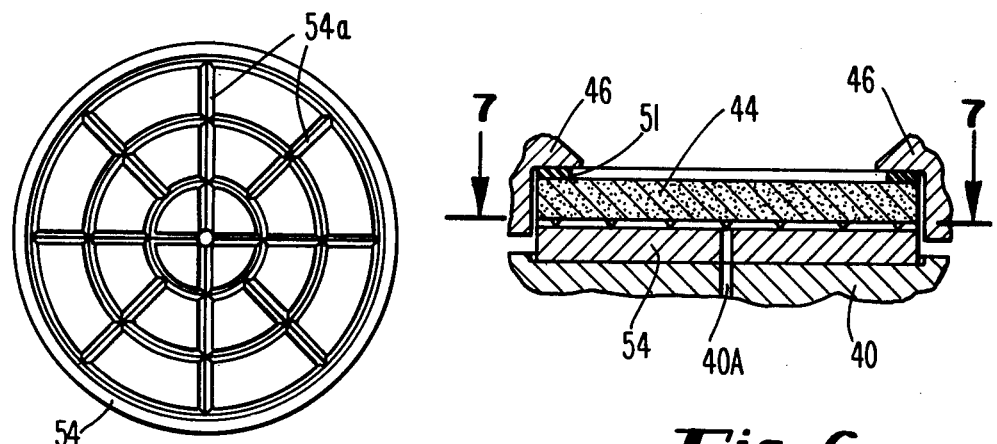
*Fig. 7*
*Fig. 6*

STICKOMETER

Field of the Invention

This invention relates to instruments for measuring the relative "stickiness" of a given substance. More particularly, the invention relates to an apparatus whereby the relative tendency of a metal drilling pipe to stick to the wall of a well being drilled can be evaluated.

Background of the Invention

Bariod Division of NL Industries sells a device known as the "Baroid Stickmeter" which is a device for making comparative measurements of the tendency for drilling fluids or "muds" to cause differential pressure sticking of the drill string to the wall of a well being drilled. It comprises a chamber for holding a piece of filter paper and a plunger for applying pressure to the filter. In use, a drilling mud being tested is placed within the chamber and is pressurized to a typical working pressure, for example, 500 psi. This forces the fluids in the mud through the filter, while the solids form a filter cake. A plunger provided with an elongated shaft extending out of the chamber is pressed against the filter cake. A torque wrench is applied to the top of the plunger and the amount of torque required to turn the plunger while pressed against the filter cake is measured. This provides a relative indication of the tendency of the mud to cause differential pressure sticking down a hole, insasmuch as the sticking mechanisms are very comparable.

As mentioned, the stickometer works by simulating the down hole environment. It would appear desirable therefore to replace the filter paper with a sandstone-like material, as this is the typical material of the formations in which wells are drilled using the mud technique. Moreover, the stickometer as furnished by Baroid provides no means of locating the position of the plunger during operation, which could yield valuable additional information such as the filter cake thickness and compressibility. The baroid instrument also does not provide any way to accurately locate the plunger a predetermined small distance away from the filter prior to filtration which might additionally simulate the down hole environment.

Object of the Invention

Accordingly, it is an object of the invention to provide an improved stickometer in which actual rock samples are used instead of filters for the building up of a filter cake so as to more accurately simulate the down hole environment.

It is also an object of the invention to provide means for accurate measurement of the position of the plunger, and for spacing the plunger a predetermined distance from the filter prior to filtration.

Summary of the Invention

The present invention satisfies the needs of the art and objects of the invention mentioned above by its provision of an improved stickometer in which the chamber is shaped so as to accommodate a circular disk of sandstone or other material of interest rather than a filter paper and its support. Rather than apply pressure to the plunger by a weight system, as was done in the prior art, an air cylinder is provided to provide pressure to the plunger. The opposite end of the air cylinder may desirably be exposed to the tip of a conventional dial indicator, thus providing an accurate indication of the travel undergone by the air cylinder and hence by the plunger upon filtration. A threaded nut is also provided to define the distance between the plunger and the filter paper prior to filtration.

Brief Description of the Drawings

The invention will be better understood if reference is made to the accompanying drawings, in which:

FIG. 5 is a cross-section along the line 5—5 of FIG. 4 and shows the details of the stickometer chamber assembly;

FIG. 6 is a fragmentary view comparable to FIG. 5 showing one possible modification of the embodiment shown in FIG. 5 and FIG. 7 is a cross-sectional view taken along the line 7—7 of FIG. 6.

Description of the Preferred Embodiments

Figure 1:
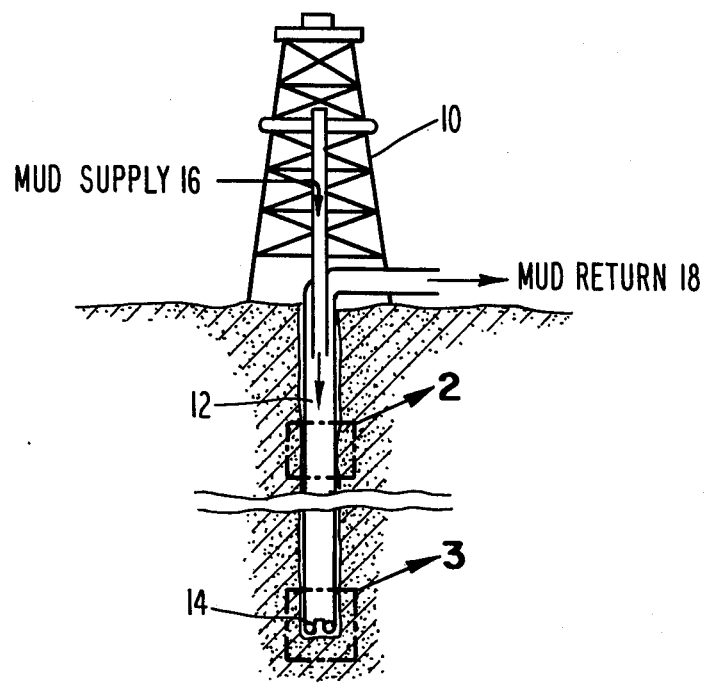
FIG. 1 shows a general layout of oil well drilling operations.

FIG. 1 shows a typical well drilling operation. A well drilling rig 10 supports a drill string comprising a length of drill pipe 12 at the bottom of which is a drill bit 14, all as is conventional in the art. The drill string 12 and the bit 14 are typically rotated and lowered to generate the drilling force. Mud is piped from a mud supply indicated at 16 down the center of the drill pipe and removes the debris in the vicinity of the drill bit in addition to cooling it, thus ensuring its longer life. The mud is pumped up around the outside of the drill string 12 and to a mud return indicated generally at 18.

Figure 3:
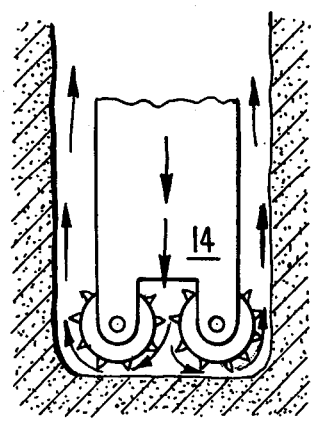
FIG. 3 shows the conditions at the bottom of the well being drilled.

FIG. 3 shows the conditions at the bottom of the hole. The end of the drill bit 14 may generally comprise a plurality of rotable cone-shaped members having chisel teeth formed or embedded therein to cut the rock when the drill bit 14 is rotated and moved down. The mud comes down the center of the tube as shown by the arrows and is pumped up around the outside of the drill bit to exit at the top of the hole as noted above.

Figure 2:
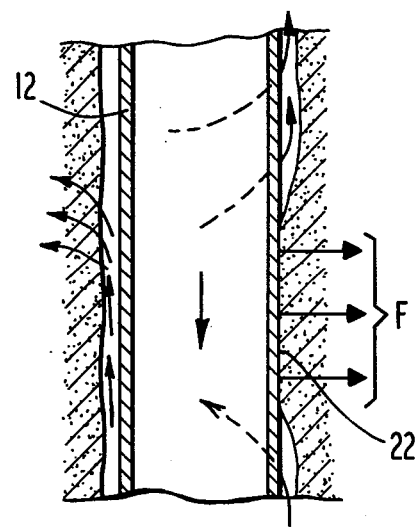
FIG. 2 shows a detail of the conditions in a central area of the well being drilled.

FIG. 2 shows conditions existing in a central region of the well. Mud around the outside of the drill pipe is under the hydrostatic pressure exerted by the column of mud from that point to the surface. The hydrostatic pressure is usually controlled to be greater than the fluid pressure in the pores of the formation. When the formation is permeable, as is common, the liquid portion of the mud will invade the pores of the formation leaving a filter cake on the wall of the hole. The difference between the hydrostatic pressure in the mud and the fluid pressure within the pores of the formation is the filtration pressure, or the differential pressure. If the pipe 12 is still, for example, to add an additional section of pipe to the drill string, and is in contact with the filter cake, the differential pressure will seal the pipe against the cake and hold it in place with a force F equal to the area of contact times the differential pressure. The tendency for the pipe to stick is a function of the characteristics of the mud and the formation.

Accordingly, it is desirable to provide a means for experimenting with various drilling muds and mud additives to determine the relative "stickiness" they exhibit in a situation such as the down hole environment pictured in FIG. 2, and this is the intent of the Baroid Stickometer. The plunger simulates the pipe, the filter paper is intended to simulate the typically porous formation of the wall of the hole and the pressure supplied to force the plunger into engagement with the filter is the analogue of the differential pressure existing in situations such as that pictured in FIG. 2.

According to the present invention, however, the filter paper used in the Baroid version of the stickometer is replaced by a disk of sandstone or other porous formation rock material to more closely simulate conditions existing in the well and to further improve the accuracy of the experimental results. As in the case of the well and in the case of the Baroid version of the stickometer, mud is supplied under pressure to the sandstone and the less viscous portions of the mud squeeze through the sandstone, leading to the accumulation of a filter cake on the surface of the sandstone, again just as occurs in the down hole situation shown in FIG. 2.

Figure 4:
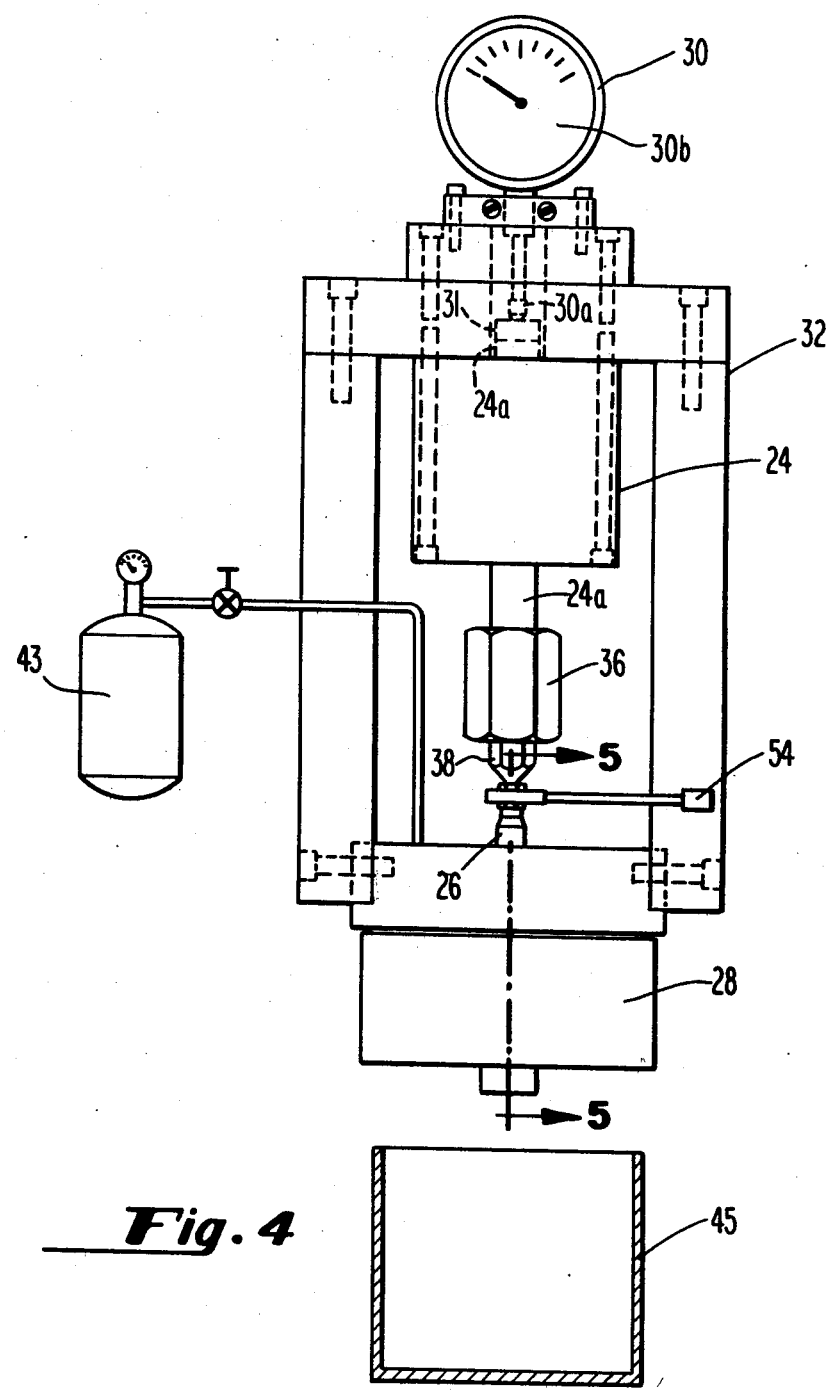
FIG. 4 shows the overall layout of the stickometer assembly, with the pressurized gas cylinder, torque wrench, and dial indicator.

FIG. 4 shows the overall layout of the apparatus for use of the improved stickometer of the invention. The apparatus shown uses an air cylinder 24 to apply pressure to the plunger 26 protruding from the stickometer cell 28. The structure shown in FIG. 4 enables control of additional experimental parameters. For example, a dial indicator 30 is provided; its movable tip 30a when displaced up and down produces a readable indication on its face 30b. Typically displacements on the order of 0.001" can be readily measured. The tip 30a of the dial indicator 30 is in contact with a nut 31 threaded to the piston 24a of the air cylinder 24. In this way when the piston of the air cylinder moves up and down, in conjunction with the plunger 26 moving up and down, the dial indicator 30 provides a direct indication of how much it has moved. This is useful, for example, in evaluation of compressibility and thickness of the filter cake formed on the sandstone disk. An additional degree of flexibility is also provided by the embodiment shown in FIG. 4. A nut 36 is threaded between the piston 24a of the air cylinder 24 and the connective 38 contacting the plunger 26. This allows the plunger 26 to be positioned a predetermined small distance above the porous filtering medium before filtering begins, thus once again simulating down hole conditions, i.e., where the drill pipe is not in direct contact with the wall of the hole, but is some finite distance away.

FIG. 5 shows a cross-sectional view along the line 5—5 of FIG. 4 and illustrates the details of the stickometer cell 28. It comprises a body portion 40 and cap 42. The plunger 26 extends through a hole in the cap 42 and can be brought into contact with the filtering medium 44 which according to the invention is generally circular disk of material comparable to that of the formation of the well, typically a sandstone. The sandstone filtering medium is clamped by a clamp member 46 which is threaded to the body of the cell 40. The clamp member 46 is provided with pins 52 so as to enable it to be tightened down with respect to the body of the cell 40. The assembly is provided with O-rings 48–50 and a gasket 51 to seal it together.

In operation drilling mud is supplied to the cavity 53 through a hole (not shown) in the cap 42 and the assembly is pressurized, typically to 500 psi, e.g. by supply of compressed gas from a cylinder 43 (FIG. 4). The typical mud comprises both fluids and solids and the fluids are forced under the pressure through the sandstone and out through a drain 40a provided in the base of the cell 40. The fluid is collected in a beaker 45 or the like (FIG. 4) for measurement. A filter cake builds up on the surface of the sandstone core 44 which is exposed to the plunger 26. The plunger 26 is then placed in engagement with this filter cake. Some additional force must be applied to the plunger so as to seal it to the filter cake since the ambient pressure is initially equal on both sides of the plunger 26. This is supplied by air cylinder 24 (FIG. 4). After the plunger 26 has been held in engagement with the sandstone disk 44 for a specified length of time, typically five minutes, allowing any incipient sticking to occur, torque is applied to the stem of the plunger by a wrench 54 (FIG. 4). The torque required to turn the plunger is recorded as one of the experimental variables. These include the volume of the fluid expelled upon pressurizing the cell, the mud composition, the stone filter source and the length of time the plunger was in engagement with the filter cake. The experimental results then can be compared with other muds, so as to determine, e.g., alternative mud compositions in case sticking is encountered, or the same mud having additional non-sticking additives mixed therein, as well known in the art.

The apparatus of the invention as shown in FIG. 4 provides additional flexibility not previously provided in instrumentation of this kind. The assembly of the cell together with the dial indicator 30 directly coupled to the plunger 26 through the air cylinder piston 24a allows one to directly read out the compressibility of the filter cake, i.e., by applying a specified amount of pressure to the air cylinder one can expect that the filter cake will be further compressed by the action of the plunger. The amount of this compression can be directly read off the dial indicator 30, and recorded as an experimental variable. The lever action weighting scheme used by Baroid to apply pressure to the plunger does not lend itself to ready measurement of the axial travel of the plunger 26. The provision of the nut 36 connecting the piston 24a and the contactor 38 can also be used to space the plunger 26 a certain distance above the filtration member 44 prior to application of pressure to the cell 28. This can provide an additional simulation feature, providing a model of the situation in which the drill pipe is close to but not in direct contact with the wall. By providing the threaded member 36 this adjustment can be made very precisely and repeatably from one experiment to the next. One would simply place the plunger in contact with the filtration medium prior to applying pressure and then use the nut 36 to back it off a predetermined distance. Control of this experimental variable is new to the art.

FIG. 6 shows an alternative embodiment of the invention in which a thinner stone filtration member 44 is used. A spacer 54 is used to take up the additional distance. FIG. 7 shows a plan view of this spacer 54, which has grooves 54a formed in its upper surface to provide drainage channels for the fluid pressed through the filtration medium 44 when pressure is applied to the cell. The inner bottom surface of the cell body 40 can be similarly formed for the same purpose.

In a preferred embodiment of the invention, the cell 40 is formed of stainless steel by machining. The sandstone core size controls most of the dimensions of the cell. In a serviceable embodiment, the sandstone disk may comprise a Berea sandstone disk 2-½ inches in diameter by ½ inch thick. The plunger 26 should have a polished lower surface for proper interaction with this filtration medium. The overall diameter of the cell member is 4 inches and at its thinnest section, just below the threads by which the cap 42 is attached, has a wall thickness of approximately 0.200". As noted above, the working pressure of this cell is 500 psi and cells of this design have been successfully tested up to 750 psi without failure.

While a preferred embodiment of this invention has been shown and described, it will be appreciated that it is within the skill of the art to make further improvements and modifications and therefore the above description of the invention should be considered exemplary only and not as a limitation on its scope, which is more properly defined by the following claims.

We claim:

1. Apparatus for the comparative measurement of the tendency of a particular drilling fluid to cause sticking of a drilling tube to the wall of a well being drilled in a rock formation comprising:
    a cell for containing samples of said fluid and of a porous rock material filtration member similar to that of the formation of the well being drilled;
    means to apply pressure to said cell to force liquid out of said drilling fluid through said porous filtration member and out of said cell so as to deposit a filter cake on said porous filtration member; and
    plunger means for being placed into engagement with said filter cake, means for applying a torque to said plunger means and means for measuring said torque so as to provide an indication of the relative adhesion of said plunger to said filter cake.

2. The apparatus of claim 1 further comprising means for measuring the amount of liquid emitted from said cell.

3. The apparatus of claim 1 further comprising means for applying a specified force to said plunger for urging it into engagement with said filter cake, and means for measuring the amount of compression undergone by said filter cake upon application of said force to said plunger.

4. The apparatus of claim 1 further comprising means for controllably spacing said plunger means from said filtration member prior to application of pressure to said cell to cause said fluids to be filtered by said filter member.

5. A method for the simulation of conditions within a well being drilled, and determination of the relative tendency of a drill pipe to adhere to the wall of the well, comprising the steps of:
    filling a cell having a stone filtration member therein with a sample of drillig mud to be used in said well;
    applying pressure to said cell to cause liquids to be transmitted through said filtration medium, whereby a filter cake is built up on said medium;
    placing a plunger in juxtaposition to said filter cake such that the pressure within said cell presses said plunger firmly against said cake;
    allowing said plunger to remain immobile with respect to said filter cake for a specified period of time;
    applying a torque to said plunger so as to rotate it with respect to said filter cake; and
    measuring the amount of torque required to cause said plunger to thus rotate.

6. The method of claim 5 further comprising the step of measuring the amount of liquid filtered from said drilling mud upon application of pressure to said cell.

7. The method of claim 5 further comprising the step of applying an axial force to said plunger to cause it to be pressed against said filter cake and measuring the amount of compression undergone by said filter cake upon applicaton of said force to said plunger.

8. The method of claim 5 further comprising the step of maintaining said plunger a specified distance from said filtration medium prior to application of pressure to said cell so as to further simulate conditions within said well.

9. A cell for the measurement of relative adhesion of a plunger to a filter cake built up on filtration means within said cell upon application of pressure to the interior of said cell to cause liquids to be filtered from a sample to be tested and a filter cake to be built up upon said filtration medium wherein the improvement comprises forming said filtration medium from an actual stone sample.

10. The cell of claim 9 wherein said measurement is intended to simulate conditions occurring in a real well being drilled and said stone is selected to be the same type of stone as that in which the well is drilled.

* * * * *